(12) United States Patent
Boyle et al.

(10) Patent No.: US 7,299,682 B2
(45) Date of Patent: Nov. 27, 2007

(54) METHOD AND APPARATUS FOR ESTIMATING BASICITY OF A USED, ALL-LOSS CYLINDER LUBRICANT

(75) Inventors: Frederick P. Boyle, Kirtland, OH (US); Vadim F. Lvovich, Cleveland Heights, OH (US); Peter V. Kampe, Newbury, OH (US)

(73) Assignee: The Lubrizol Corporation, Wickliffe, OH (US)

( * ) Notice: Subject to any disclaimer, the term of this patent is extended or adjusted under 35 U.S.C. 154(b) by 103 days.

(21) Appl. No.: 11/250,274

(22) Filed: Oct. 14, 2005

(65) Prior Publication Data

US 2007/0084271 A1    Apr. 19, 2007

(51) Int. Cl.
*G01R 27/08* (2006.01)
*G01N 33/26* (2006.01)

(52) U.S. Cl. .................. 73/53.05; 324/693; 324/698
(58) Field of Classification Search .............. 73/53.05; 324/693, 691, 698; 702/30
See application file for complete search history.

(56) References Cited

U.S. PATENT DOCUMENTS

| | | | | |
|---|---|---|---|---|
| 4,741,204 A | * | 5/1988 | Luck et al. | .................. 73/116 |
| 5,067,455 A | * | 11/1991 | Okajima et al. | ......... 123/196 R |
| 6,779,505 B2 | | 8/2004 | Reischman et al. | ..... 123/196 R |
| 6,844,745 B1 | * | 1/2005 | Schachameyer et al. | .... 324/698 |
| 7,043,372 B2 | * | 5/2006 | Koehler et al. | ............... 702/25 |
| 2002/0125899 A1 | | 9/2002 | Lvovich et al. | ............. 324/698 |
| 2003/0164451 A1 | | 9/2003 | Reischman et al. | .... 250/339.12 |
| 2004/0144355 A1 | | 7/2004 | Carey et al. | ............ 123/196 R |

FOREIGN PATENT DOCUMENTS

EP    0901011 B1    12/1998

OTHER PUBLICATIONS

Smiechowski M.F. et al., "Iridium Oxide Sensors for Acidity and Basicity Detection in Industrial Lubricants", (Sensors and Actuators B vol. 96, No. 1-2 Nov. 15, 2003, pp. 261-267).
Corresponding International Application No. PCT/US2006/040116 Search Report mailed Feb. 26, 2007.

* cited by examiner

*Primary Examiner*—Hezron Williams
*Assistant Examiner*—Tamiko Bellamy
(74) *Attorney, Agent, or Firm*—Teresan W. Gilbert

(57) ABSTRACT

A method and apparatus for determining the total base number of a used lubricant from an open, all loss, lubricating system. An AC voltage signal is applied between electrodes immersed in the used lubricant and a used-lubricant dependent response to the applied signal measured. The used lubricant base number is determined from the response. To allow for changes in the fresh lubricant inputted to the open lubricating system, the method and apparatus can have means for determining properties of the fresh lubricant needed to determine the total base number of used lubricant. To allow for possible contamination of the used lubricant, the method and apparatus can have means for determining the concentration of contamination and for determining properties of the contaminant needed to determine the total base number of used lubricant.

25 Claims, 5 Drawing Sheets

| Cyl. Lub. % Sys. | TBN 4 | | | TBN 40 | | | TBN 75 | | |
|---|---|---|---|---|---|---|---|---|---|
| | Meas. (MΩ) | Mix. (MΩ) | R.N. (MΩ) | Meas. (MΩ) | Mix. (MΩ) | R.N. (MΩ) | Meas. (MΩ) | Mix. (MΩ) | R.N. (MΩ) |
| 0 | 45 | 45 | 45 | 6.0 | 6.0 | 6.0 | 4.0 | 4.0 | 4.0 |
| 1 | 44 | 45 | 44 | 5.8 | 6.0 | 5.9 | 3.9 | 4.0 | 3.9 |
| 10 | 35 | 43 | 37 | 5.0 | 6.3 | 5.0 | 3.2 | 4.1 | 3.3 |
| 25 | 27 | 35 | 30 | 4.0 | 6.4 | 4.0 | 2.6 | 4.1 | 2.7 |
| 50 | 18 | 30 | 22 | 3.0 | 7.2 | 3.0 | 2.0 | 4.8 | 2.0 |
FIG. 9
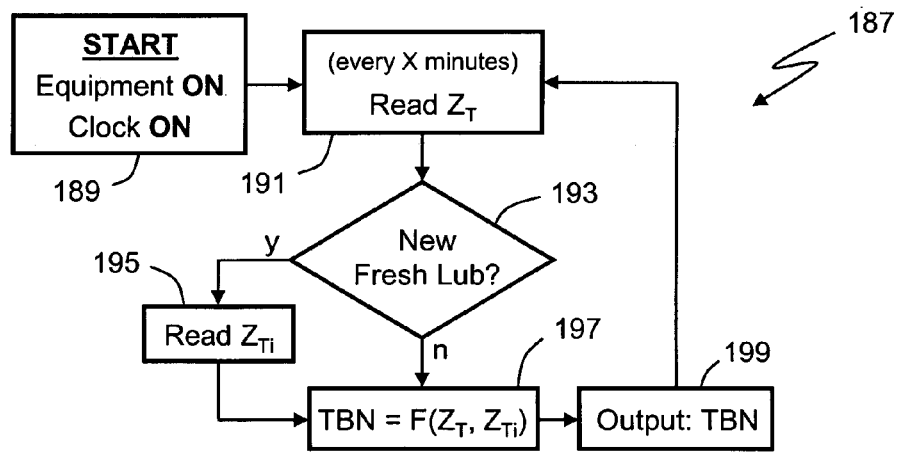
FIG. 10
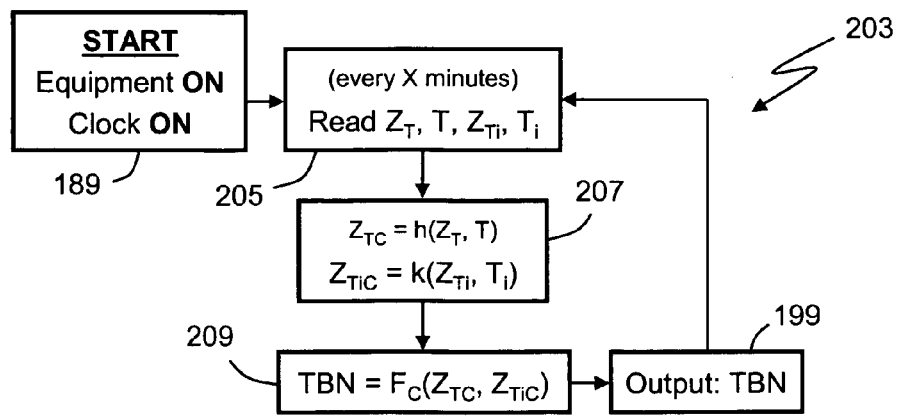
FIG. 11

METHOD AND APPARATUS FOR ESTIMATING BASICITY OF A USED, ALL-LOSS CYLINDER LUBRICANT

BACKGROUND OF THE INVENTION

The present invention is a method and apparatus for determining remaining basicity of a used cylinder lubricant from an open, also referred to as an all-loss, lubrication system. The present invention has benefit in providing a near real-time basicity estimate of the used lubricant from an open power-cylinder lubricating system of a slow-speed, two-stroke diesel engine of crosshead construction.

Slow-speed, two-stroke diesel engines of crosshead construction are used in marine propulsion, stationary power or other applications because of their efficient, high power output. Unlike a smaller four-stroke engine with a single closed lubricating system that continuously circulates lubricant from a reservoir, often referred to as a sump, to the engine components and back to the reservoir, the crosshead two-stroke engine has two lubricating systems, a closed recirculating system that lubricates and protect the surfaces in the crankcase, and an open system that applies a cylinder lubricant only once to lubricate and protect the power cylinder walls and pistons before the used lubricant is removed from the engine and discarded.

A major reason for using an open cylinder lubricating system is that sulfur content of fuel for slow-speed crosshead engines is typically in the range of 1.5 to 5.0%. This compares to fuel sulfur content of typically less than 0.05% for most medium and high speed diesel engines. Since sulfur reacts to form acids, especially during the combustion process, the higher sulfur content fuel results in higher acid content in the engine cylinders. If the acids formed during combustion are not effectively neutralized, they can attack engine surfaces to cause reduced engine performance and life. Lubricant used on internal-combustion-engine cylinder walls should, as one of is functionalities, neutralize acids. This neutralizing functionality is achieved by formulating the lubricant to have high alkalinity, that is, to be highly basic. A lubricants' alkalinity is described by a Total Base Number (TBN), often referred to as the lubricant's Base Number (BN), which is a measure of the amount of acid that a mass of lubricant can neutralized. TBN is reported in terms of milligrams of potassium hydroxide per gram (mg KOH/g) and is, in general, determined by either ASTM D2896 or D4739 titrations methods. The sulfur content of typical four-stroke diesel fuel is sufficiently low so that a sufficiently high TBN engine lubricant can be formulated to allow a relatively long useful life in a closed lubricating system. Lubricant useful life ends and the lubricant must be replaced when the remaining TBN reaches a limit, typically set by the engine manufacturer, below which the lubricant no longer provides the desired acid neutralization function. With the high sulfur content of slow-speed crosshead diesel engine fuel, a lubricant has not been formulated to have a long service life in a closed lubricating system; hence an open lubricating system should be used.

To provide desired engine performance and life at an acceptable cost, the formulation and flow rate of a lubricant in an open cylinder lubricating system needs to be optimized. The lubricant flow rate should be selected to be sufficiently high for a particular engine operating condition to provide a lubricating film to minimize friction between piston rings and cylinder walls, and the lubricant must be formulated so that at a selected flow rate and operating condition and at a given fuel sulfur content, there is an appropriate basicity to adequately neutralize acids entering the lubricant from the combustion process without having excess basicity that can cause piston ring deposits and ultimately ring and cylinder wall wear. Appropriate basicity is typically determined by the remaining TBN of the used cylinder lubricant that is removed from a cylinder.

Traditionally, the optimization of lubricant flow rate and formulation is done by selecting a lubricant with an appropriate TBN for an expected range of fuel sulfur contents and varying lubricant flow rate to the cylinders based on a table or formula that uses the actual sulfur content reported by the fuel supplier, the operating condition/state of the engine, and historic off-line TBN analyses of used cylinder lubricants. The TBN analyses are typically laboratory methods performed on samples removed from individual cylinders for known fuel sulfur content and operating conditions. A problem with this traditional optimization method is that the current flow rate decision is made based on historic TBN data and not real-time or near real-time data. Hence, flow rates are, in general, conservatively set higher than needed so as to protect against, for example, transient or incorrectly reported fuel sulfur content. While a too high flow rate is better than the consequences of having a too low flow rate, a too high flow rate results in added lubricant costs and can potentially lead to piston ring deposits.

To minimize both risks and costs, engine operators desire to know the remaining TBN in the used cylinder lubricant in either real-time or near real-time to set an appropriate lubricant flow rate. Methods that use acid reagents to measure or estimate TBN, such as the ASTM methods, are too complex in most engine applications to be accurately and/or quickly performed. Methods that use Infrared (IR) Spectroscopy to measure one or more oxidation peaks of the used lubricant, for example the method described in Reischman et al. U.S. Patent Application 2003/0164451, currently estimate TBN by near real-time methods. An issue with IR TBN sensors is that due to the relatively opaque nature of used cylinder lubricant the sensor must have a relatively narrow gap if a transmission technique is used or must use an Attenuated Total Reflectance (ATR) technique. A narrow gap of a transmission IR sensor can get blocked over long periods with the relatively high viscosity used lubricant, and a surface of an Internal Reflection Element (IRE) of an ATR IR sensor can get coated over long periods with the relatively high viscosity, surface active used lubricant. When used in situ for essentially real-time TBN estimates, IR sensors typically require periodic cleaning to assure accurate long-term results.

Another issue when determining the remaining TBN of a used cylinder lubricant is that the used lubricant can be contaminated by the system lubricant in the closed lubrication system that lubricates the engine's crankcase components. The crosshead construction of two-stroke engines has a diaphragm and stuffing boxes separating the power cylinders from the crankcase to prevent combustion by-products and cylinder lubricant from entering the crankcase and conversely to prevent crankcase lubricant from entering the cylinder and mixing with the used cylinder lubricant before removal from the engine. The diaphragm and stuffing boxes, however, are typically not 100% efficient and, in general, the efficiency decreases with engine use such that the lubricant removed from the power cylinders may be a mixture of used cylinder lubricant and crankcase lubricant with the ratio of the two lubricants varying with engine operating conditions. Hence, the measured TBN may not accurately represent the TBN of the used cylinder lubricant.

Therefore, there remains a need for a reliable, accurate method and apparatus for real-time or near real-time estimation of used cylinder-lubricant remaining TBN over long periods of use. Accordingly the present invention is a method that meets that need.

SUMMARY OF THE INVENTION

The present invention relates to a method and apparatus for determining the remaining basicity of a used lubricant from an open, lubrication system. More specifically, the invention relates to a method and apparatus that can be used in situ to provide an essentially real-time or near real-time determination of the TBN of the used lubricant from an open, all loss, power-cylinder lubricating system of a slow-speed, two-stroke diesel engine of crosshead construction.

The invention includes the steps of applying an AC electrical potential across the used lubricant, measuring the resulting electrical response and determining the used lubricant base number from the measured response to the applied potential.

The method can further include measuring the used lubricant temperature.

The method can further include compensating the lubricant response for variations in lubricant temperature.

The method can further include the step of changing the temperature of the used lubricant to a desired temperature before applying the electrical potential and measuring the resulting electrical response.

The method can further include the steps of using at least one of the following, using the total impedance of the fresh lubricant, using the TBN of fresh lubricant, applying a second AC electrical potential across the fresh lubricant and using a measured second electrical response of the fresh lubricant at a fixed or compensated temperature, or combinations thereof in the determination of the used lubricant base number.

The method can further include the step of determining the concentration of contaminant in the used lubricant in the determination of the used lubricant base number.

The method can further include the steps of measuring the flow rate of the used lubricant exiting the open lubricating system and comparing that to the flow rate of the fresh lubricant entering the open system to determine the concentration of contaminant in the used lubricant.

The method can further include the step of using the electrical response of the contaminant, the system lubricant in the case of a slow-speed, two-stroke diesel engine of crosshead construction, to a third applied AC electrical potential across the lubricant at a fixed or compensated temperature in the determination of the used cylinder lubricant's base number.

In another aspect of the invention, the electrical response is the current resulting from the applied AC electrical potential.

In another aspect of the invention, the base number of the used lubricant can be determined using electrical impedance value(s) calculated from measured electrical response(s) to applied electrical potential(s).

In accordance with another aspect, the present invention further includes a monitoring apparatus having at least a pair of separated electrodes that are immersed in the used lubricant being analyzed, at least one signal generator that applies to the electrodes an AC electrical potential, at least one monitor that measures an electrical response to the applied potential, and a controller that analyzes the measured electrical response to the applied electrical potential to determine the base number of the used lubricant.

In another aspect of the invention the monitor(s) is a current sensor, which measures a current generated in response to the applied potential.

In another aspect of the invention, the apparatus can further include a temperature sensor that monitors the temperature of the used lubricant.

In another aspect of the invention, the apparatus can further include means for compensating the base number determination for variations in lubricant temperature(s).

In another aspect of the invention, the apparatus can further include temperature control means for regulating the temperature of lubricant(s) being monitored.

In another aspect of the invention, the apparatus can further include means for determining if properties of the fresh lubricant before use have changed since the last determination when determining the base number of the used lubricant.

In another aspect of the invention, the apparatus can further include at least one pair of separated electrodes that are immerse in the fresh lubricant before use, at least one signal generator that applies to the electrodes in the fresh lubricant an AC electrical potential, at least one monitor that measures an electrical response of the fresh lubricant to the applied potential for use when determining the used lubricant base number.

In another aspect of the invention, the apparatus can further include means for determining the amount, that is the concentration, of a contaminant in the used lubricant when determining the base number of the used lubricant.

In another aspect of the invention, the apparatus can further include at least one flow rate means for comparing the fresh lubricant input to the open lubricating system to the used lubricant output to determine the amount of any contaminant that may be present, for use when determining the used lubricant base number.

In another aspect of the invention, the apparatus can further include means for determining properties of a potential contaminant, for use when determining the base number of the used lubricant.

In another aspect of the invention, the apparatus can further include at least one pair of separated electrodes that are immersed in the potential contaminant, at least one signal generator that applies to the electrodes in the potential contaminant an AC electrical potential, at least one monitor that measures an electrical response of the potential contaminant to the applied potential for use when determining the base number of the used lubricant.

In another aspect of the invention, the apparatus can further include at least one temperature sensor that monitors the potential contaminant temperature.

In another aspect of the invention, the apparatus can further include temperature control means for regulating the temperature of a potential contaminant responding to an applied electrical signal.

The present invention may be more readily apparent from the following figures.

BRIEF DESCRIPTION OF THE FIGURES

FIG. 9 is a table comparing the measured total impedances of contaminated used lubricant with values calculated by two methods as a function of percentage contamination.

FIG. 10 is a flow chart of a feature of a method of the present invention wherein measured used lubricant total impedance is used to determine the used lubricant TBN.

FIG. 11 is a flow chart of a feature of a method of the present invention wherein measured used lubricant total impedance and fresh lubricant total impedance are temperature compensated and used to determine the used lubricant TBN.

DETAILED DESCRIPTION OF THE INVENTION

The invention relates to a method and apparatus for determining the base number of a used lubricant from an all-loss lubricating system. In particular, the invention relates to a method and apparatus for determining in real-time or near-real-time the base number of the used lubricant from an open power-cylinder lubricating system of a slow-speed, two-stroke diesel engine of crosshead construction.

Figure 1:
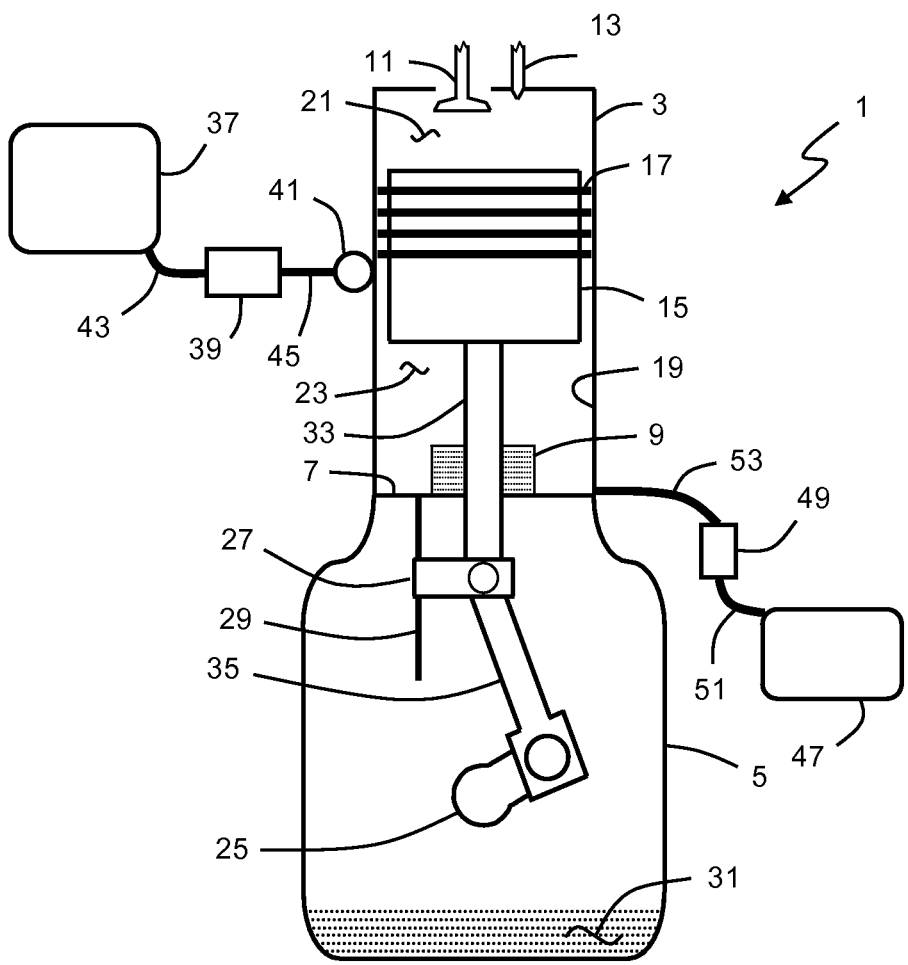
FIG. 1 is a schematic representation of one cylinder of a slow-speed, two-stroke diesel engine of crosshead construction.

FIG. 1 is a schematic cross section of a slow-speed, two-stroke diesel engine 1 of crosshead construction. Engine 1 includes cylinder 3 and crankcase 5. One end of cylinder 3 is separated from crankcase 5 by separation plate 7 with stuffing box 9, and the other end has valve 11 and fuel injector 13. Cylinder 3 includes piston 15 with rings 17 with the outer diameters in close proximity with the surface 19 of the cylinder effectively separating volumes 21 and 23 of cylinder 7. Crankcase 5 includes crankshaft 25, crosshead 27 with crosshead guide 29 and system lubricant 31. Piston 15 is connected to crankshaft 25 through upper connecting rod 33, which passes through separation plate 7 and stuffing box 9, crosshead 27 and lower connecting rod 35. Engine 1 also includes cylinder lubricant reservoir 37, cylinder lubricant day reservoir 39, injection pump 41, conduit 43 that communicates lubricant from reservoir 37 to reservoir 39 and conduit 45 that communicates lubricant from reservoir 39 to pump 41. Engine 1 also includes used cylinder lubricant reservoir 47, diagnostic chamber 49, conduit 51 that communicates used lubricant from chamber 49 to reservoir 47, and conduit 53 that communicates used lubricant from volume 23 of cylinder 7 to diagnostic chamber 49.

In operation, crankshaft 25 of engine 1 is rotated by energy released by combustions in volume 21 as is well known in the art. In particular, energy from crankshaft 25 is used to raise piston 15, through connecting rods 33 and 35 from the lowest position that the crankshaft allows, and as piston 15 rises in cylinder 3, valve 11 opens briefly allowing air to be quickly pumped into volume 21. The air in volume 21 is compressed, thereby increasing in temperature, as the piston continues to rise, and at a predetermined position near the top of the stroke of piston 15, injector 13 sprays fuel into volume 21 where combustion releases energy forcing piston 15 to the opposite end of cylinder 3 and turning crankshaft 25 through connecting rods 33, 35. The exhaust gasses from the combustion are exhausted through vents (not shown) and the cycle repeats. During engine 1 operation injection pump 41 injects a controlled amount of fresh cylinder lubricant from reservoir 39 onto surface 19 of cylinder 3 with each stroke of piston 15. The cylinder lubricant minimizes degradation of surface 19 and rings 17 by a variety of mechanism including providing a lubricating film and neutralizing the acids formed during the combustion process. As piston 15 oscillates in cylinder 3 used cylinder lubricant flows from surface 19 by gravity and or by the urging of piston rings 17 onto separation plate 7. Conduit 53 communicates the used lubricant from separation plate 7 to diagnostic chamber 49 and conduit 53 communicates the used lubricant to reservoir 47. Also during engine 1 operation system lubricant 31 is pumped, typically through one or more filters and/or water separators (not shown) onto engine components in the crankcase for lubrication and cooling. Any system lubricant 31 that covers the portion of upper connecting rod 33 that is below separation plate 7 is, under normal operation, wiped from the rod by stuffing box 9 before entering cylinder 3.

While FIG. 1 shows only a single cylinder 3 of engine 1, an engine can have multiple cylinders with multiple pistons 15, injection pumps 41, day reservoirs 39 and diagnostic chambers 49. While day reservoir 39 is shown receiving fresh lubricant from a single lubricant reservoir 37, day reservoir 39 can receive a fresh lubricant that is a blend of fluids from multiple tanks.

Figure 2:
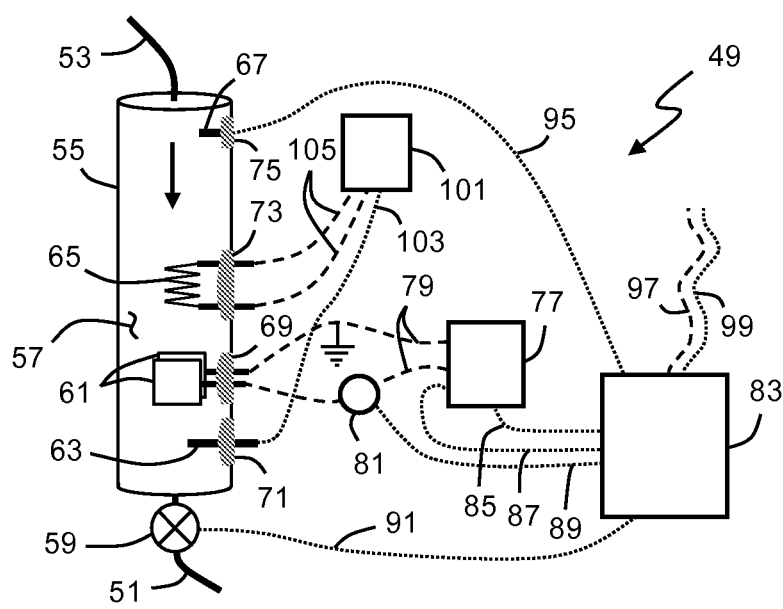
FIG. 2 is a schematic representation of one embodiment of an apparatus of the present invention that applies a potential to and measures a response of a used lubricant to determine the base number of the used lubricant, wherein the apparatus controls used lubricant temperature.

FIG. 2 is a schematic illustration of an embodiment of apparatus 49 of the present invention for determining the base number of used cylinder lubricant. Apparatus 49 includes diagnostic chamber 55 with volume 57 that receives lubricant through conduit 53 from the 2-stroke engine cylinder 3 shown in FIG. 1. The lubricant is, in general, used cylinder lubricant; but, as previously described, may contain some system lubricant contamination due to leakage past stuffing box 9. Apparatus 49 includes valve 59 that can be controlled to block or allow used lubricant in volume 57 to flow through conduit 51 as also shown in FIG. 1. Contained in diagnostic chamber 55 are essentially parallel electrodes 61, thermocouple 63, heater 65 and level switch 67 that are fixedly held and electrically isolated by mounts 69, 71, 73, and 75 respectively. Apparatus 49 also includes signal generator 77 that supplies a voltage signal of fixed amplitude and frequency through electrical conduits 79 to electrodes 61. The voltage signal supplied by signal generator 77 is essentially sinusoidal oscillating about zero volts with the number of complete oscillations per time being the frequency of the signal. The frequency of signal generator 77 is preset based on the geometry of electrode pair 61, the temperature or temperature range, and the type of the used lubricant in volume 57. In general, the required frequency increases as a function of the electrode area divided by the separation of electrodes 61. The frequency also increases as a function of the temperature of lubricant in volume 57. In one embodiment for a used cylinder lubricant, at an operating temperature in the range from about 20° C. to about 60° C., using essentially parallel-plate electrodes with an area to gap ratio of about 300 cm, the preset high frequency of signal generator 77 is on the order of about 10 Hz. In general, the frequency of signal generator 77 is in the range of about 0.1 to about 1000 Hz for typical electrode geometries, temperature ranges and types of lubricant. Again referring to FIG. 2, one electrical conduit 79 of signal generator 77 is grounded for a voltage reference and the other conduit 79 includes a current sensor 81, which measures electrical current flow through conduit 79. Apparatus 49 also includes controller 83 with electrical conduit 85 for powering signal generator 77, electrical conduit 87 for monitoring output voltage of signal generator 77, electrical conduit 89 for monitoring current flow measured by current sensor 81, electrical conduit 89 for powering valve 59 and electrical conduit 95 for monitoring the output of level switch 67. Controller 83 also has electrical conduit 97 to receive power and electrical conduit 99 to communicate information either to or from the controller 83. Apparatus 49 also includes temperature controller 101 with electrical conduit 103 to monitor thermocouple 63, and conduits 105 to power heater 63.

In operation, valve 59 of apparatus 49 is normally open such that used cylinder lubricant is urged by gravity from engine cylinder 7 of FIG. 1 through conduit 53 into volume 57 of diagnostic chamber 55, in the direction shown by the arrow, and out the conduit 51 to used lubricant reservoir 47 of FIG. 1. The used lubricant flow rate is sufficiently low and conduits 51 and 53, valve 59 and chamber 55 are sufficiently large so that chamber 55 contains very little lubricant when valve 59 is open. To determine the TBN of the used cylinder lubricant, controller 83 powers valve 59, through electrical conduit 91 to close at time zero. With valve 59 closed, used lubricant fills volume 57. Temperature controller 101, through electrical conduit 103 monitors the temperature of the lubricant in volume 57 with thermocouple 63 and applies power through electrical conduits 105 to maintain a preset temperature of lubricant in volume 57. Controller 83, through electrical conduit 95, determines the time since valve 59 closes to when the lubricant in chamber 55 reaches level switch 67 and with the known volume of chamber 55 below switch 67 calculates the flow rate of the used lubricant from cylinder 3 of FIG. 1. When the level of used lubricant reaches switch 67, controller 83 powers signal generator 77 through electrical conduit 85 to apply a signal through conduits 79 and electrodes 61 to used cylinder lubricant between the electrodes. The electrical response of the used lubricant to the applied signals causes current to flow, which is measured by current sensor 81. Controller 83 monitors, using electrical conduits 87, 89, the applied signal and the corresponding current flow respectively, and from the voltage and current signals calculates impedance of the used lubricant. Controller 83 receives information through electrical conduit 99 of the flow rate of cylinder lubricant into cylinder 3 through injection pump 41 of FIG. 1 and calculates the ratio of the flow rate into the cylinder to the calculated flow rate out of the cylinder. A method of this invention uses the impedance data, the flow rate ratio and the known TBN, total impedance, or both TBN and total impedance of the fresh cylinder lubricant, that is the cylinder lubricant before use, and the impedance of system lubricant 31 of FIG. 1, which may be information received by controller 83 through conduit 99, to determine the TBN of the used cylinder lubricant. A method of this invention can communicate information about the TBN of the used lubricant from controller 83 through electrical conduit 99. The TBN information can be immediately communicated to a signaling device, for example a digital output, to inform an equipment operator, to a central maintenance facility to notify remote maintenance personnel, or to a signal processor that can convert the information to other output, for example a signal that controls inject pump 41 of FIG. 1 or that controls a blender that can vary the TBN of the cylinder lubricant injected by pump 41 to maintain the TBN of the used cylinder lubricant. The TBN information can be stored in memory where it can later be retrieved. In any case, after controller 83 monitors the voltage and current needed to calculate the used lubricant impedance, controller 83 turns signal generator 77 "off" and removes power to valve 59 returning the valve to the normally open state and allowing the used lubricant to drain through conduit 51 into reservoir 47 of FIG. 1. Diagnostic chamber 55 of apparatus 49 then remains essentially empty until the next time controller 83 powers valve 59 to close to begin the next used lubricant TBN determination cycle. Controller 83 can begin TBN determination cycles either automatically or when signaled to begin the cycle through electrical conduit 99.

While FIG. 2 shows electrodes 61 to be flat rectangles with essentially only one surface of each electrode applying a signal from a signal generator to the fluid between the electrodes, in another apparatus embodiment the electrodes can have other geometry including but not limited to, concentric-cylinders, flat with a multitude interdigitated finger-like sections, and multiple surfaces, or surface sections, which may or may not directly face surface sections of the other electrode, and the like.

FIG. 2 shows apparatus with no communication between temperature controller 101 and controller 83. In another embodiment the apparatus can have communication between the two controllers such that the method of this invention can use temperature information when determining used lubricant TBN or so that information about required lubricant temperature can be communicated to the temperature controller 101.

FIG. 2 shows the electronic components of the apparatus, which apply signals and analyze the TBN of the used cylinder lubricant located with diagnostic chamber 55. In another embodiment the electronic components can be located separate from the diagnostic chamber. FIG. 2 shows apparatus components, in particular the electronic components, as individual components. In another embodiment the apparatus components can be integrated into a compact package, which, for example could reduce cost, size and/or power requirements. In another embodiment, the apparatus components can be incorporated into a package with other components, for example other lubricant sensors and/or other engine sensors that either can work in conjunction with or independent of the components of this invention.

FIG. 2 shows apparatus of this invention to be located in a diagnostic chamber 49 that uses a valve and a timing device to measure the flow rate of the used cylinder lubricant. In another embodiment, the apparatus of this invention can be located in a diagnostic chamber that uses a flow meter to measure the flow rate of used lubricant from cylinder 3 for testing in the chamber.

Figure 3:
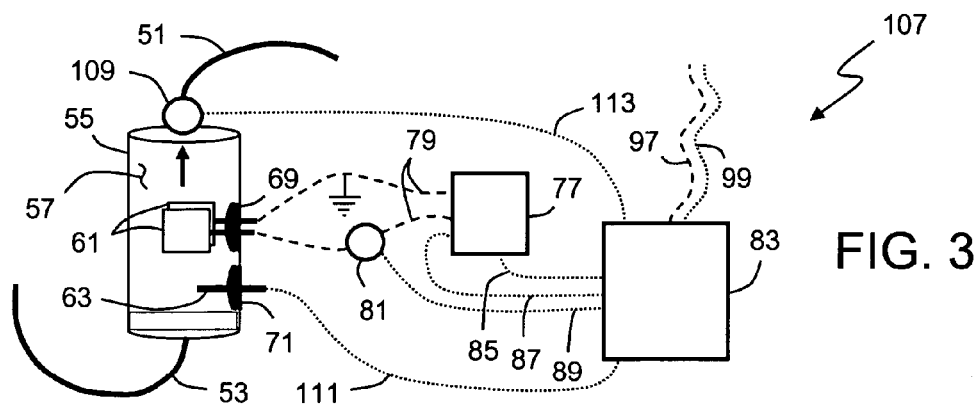
FIG. 3 is a schematic representation of one embodiment of an apparatus of the present invention that applies a potential to and measures a response of a used lubricant to determine the base number of the used lubricant, wherein the used lubricant temperature is monitored but not controlled.

FIG. 3 is a schematic illustration of another embodiment of apparatus 107 of the present invention for determining the base number of used cylinder lubricant. For convenience, apparatus elements with the same function as shown in FIG. 2 are numbered the same. Apparatus 107 includes diagnostic chamber 55 with volume 57 and flow meter 109. Chamber 55 receives used lubricant urged by gravity from conduit 53. Used lubricant exits chamber 55 via conduit 51 and due to the placement and sizing of chamber 55 and conduits 51 and 53, volume 57 is constantly filled with used lubricant. Contained in chamber 55 of diagnostic apparatus 107 are essentially parallel electrodes 61 and thermocouple 63 that are fixedly held and electrically isolated by mounts 69 and 71 respectively. Apparatus 107 also includes signal generator 77 that supplies an AC voltage signal of fixed amplitude and frequency through electrical conduits 79 to electrodes 61. One electrical conduit 79 of signal generator 77 is grounded for a voltage reference and the other conduit 79 includes a current sensor 81, which measures electrical current flow through the conduit. Apparatus 107 also includes controller 83 with electrical conduit 85 for powering signal generator 77, electrical conduit 87 for monitoring output voltage of signal generator 77, electrical conduit 89 for monitoring current flow measured by current sensor 81, electrical conduit 111 for monitoring temperature measured by thermocouple 63 and electrical conduit 113 for monitoring the used lubricant flow rate measured by flow meter 109.

In operation, volume 57 of diagnostic chamber 55 is filled with used lubricant that is discharged from engine cylinder 7 of FIG. 1 with the lubricant discharge rate measured by flow meter 109. To determine the TBN of the used cylinder lubricant, controller 83 powers signal generator 77 through electrical conduit 85 to apply a signal through conduits 79 and electrodes 61 to used cylinder lubricant between the electrodes 61. The electrical response of the used lubricant to the applied signals causes current to flow, which is measured by current sensor 81. Controller 83 monitors, using electrical conduits 111, 113, the used lubricant temperature and flow rate respectively. Controller 83 monitors, using electrical conduits 87, 89, the applied voltage signal and the corresponding current flow respectively, and calculates the impedance of the used lubricant. Controller 83 receives information through conduit 99 of the flow rate of cylinder lubricant into cylinder 3 through injection pump 41 of FIG. 1 and calculates the ratio of flow rate into the cylinder to the flow rate out of the cylinder measured by flow meter 109. A method of this invention uses the impedance data, the flow rate ratio, the lubricant temperature and the known TBN, impedance, or TBN and impedance of the fresh cylinder lubricant and the impedance of system lubricant 31 of FIG. 1 to determine the TBN of the used cylinder lubricant. The method of this invention can communicate information about the used lubricant from controller 83 through electrical conduit 99 as described for diagnostic chamber 49 of FIG. 2. Controller 83 can determine TBN of a used lubricant either automatically or when signaled through electrical conduit 99 or when powered "on" through conduit 97. If controller 83 determines used lubricant TBN automatically then the determination can be intermittent or essentially continuous. Controller 83 can essentially continuously monitor the TBN of the used cylinder lubricant passing through volume 57 by essentially continuously powering signal generator 77 to apply signals to electrodes 61 and essentially continuously monitoring the used lubricant temperature with thermocouple 63, the used lubricant flow rate with flow meter 109, the applied signal from signal generator 77 and the current flow with current sensor 81.

FIG. 3 shows apparatus 107 that includes thermocouple 63 to measure the temperature of the used lubricant. In applications where the average lubricant temperature is relatively constant, preferably varying less than 2° C., and most preferably varying less than 1° C., in another invention embodiment apparatus need not have thermocouple 63 and controller 83 does not need to monitor the temperature of the lubricant as electrodes 61 apply a signal to the lubricant. Similarly, if the used lubricant temperature is known by other means, in another embodiment of the invention apparatus, information about the used lubricant temperature can be communicated to controller 83 through, for example, electrical conduit 99 without need for thermocouple 63.

FIGS. 2 and 3 show apparatus embodiments with means to monitor the used lubricant flow rates. In apparatus 49, flow rate is measured by the time required to fill volume 57 to level switch 67, and in apparatus 107 the flow meter 109 is used to measure the flow rate. A method of the present invention uses the ratio of the flow rate of used lubricant exiting cylinder 3 to the flow rate of fresh lubricant being added to cylinder 3 by injection pump 41 of FIG. 1 to determine if the used lubricant is contaminated by another fluid and the concentration, that is percentage, of contaminate. In particular, for the 2-stroke engine case, the contaminant could be system lubricant 31 that gets past stuffing box 9 of FIG. 1. Other means can be used to determine if a contaminant is present and the concentration. For example, the contaminant could contain a marker, wherein another apparatus embodiment could include a sensor that detects the presence and concentration of the marker. The marker contained by the contaminant could be a chemical or element added specifically to the contaminant as a marker, or could be a chemical or element that is a functional part of the contaminant. For the 2-stroke engine case, X-ray fluorescence (XRF) could be used to detect zinc, an element often present in a system lubricant additive, in the used cylinder lubricant to determine the concentration of system lubricant contaminant. In applications of the present invention where the used lubricant cannot be contaminated by another fluid, or if the concentration of contamination can be measured by other means, either off- or on-line, separate from the invention apparatus and communicated to controller 83 through, for example, electrical conduit 99, then in another apparatus embodiment, the diagnostic chamber does not require means to measure the used lubricant flow rate.

FIGS. 2 and 3 show schematic illustrations of apparatus where information about the TBN, the total impedance, or both the TBN and total impedance of the fresh cylinder lubricant is either fixed or communicated to controller 83 through electrical conduit 99 from a source independent of the embodiments. Information about the fresh cylinder lubricant, however, does not have to be fixed or inputted to the controller. Methods of the present invention can measure the impedance of the fresh cylinder lubricant and use the measured impedance in the determination of the used cylinder lubricant TBN.

Figure 4:
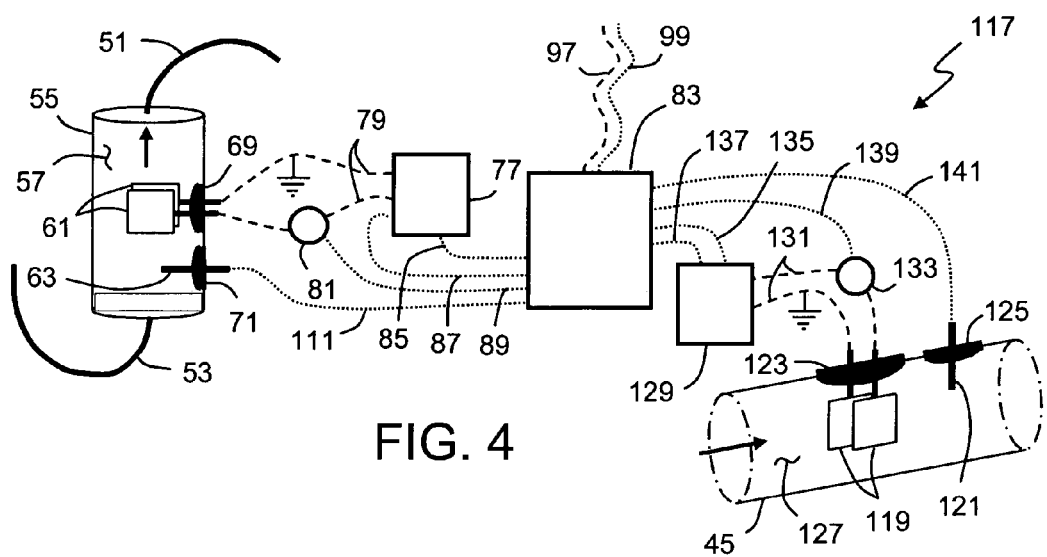
FIG. 4 is a schematic representation of one embodiment of an apparatus of the present invention that applies a first potential to and measures a first response of a fresh lubricant before use and applies a second potential to and measures a second response of the lubricant after use to determine the base number of the used lubricant, wherein the fresh lubricant temperature and the used lubricant temperature are monitored but not controlled.

FIG. 4 is a schematic illustration of another embodiment of apparatus 117 of the present invention for determining the base number of a used lubricant from an open lubrication system. For convenience, apparatus elements with the same function as shown in FIG. 3 are numbered the same. Apparatus 117 includes diagnostic chamber 55 with volume 57 that receives and is constantly filled with used lubricant urged by gravity from conduit 53. Used lubricant exits chamber 55 via conduit 51. Chamber 55 contains essentially parallel electrodes 61 and thermocouple 63 that are fixedly held and electrically isolated from reservoir 55 by mounts 69 and 71 respectively. Signal generator 77 supplies a voltage signal of fixed amplitude and frequency through electrical conduits 79 to electrodes 61 with one conduit 79 grounded for a voltage reference and the other conduit 79 includes a current sensor 81, which measures electrical current flow through the conduit. Apparatus 117 includes essentially parallel electrodes 119 and thermocouple 121 that are fixedly held and electrically isolated by mounts 123 and 125 respectively in conduit 45 of FIG. 1. Conduit 45 has volume 127 that is filled with fresh cylinder lubricant as the lubricant is urged by pump 41 into cylinder 3 shown in FIG. 1. Apparatus 117 includes signal generator 129 that supplies a voltage signal of fixed amplitude and frequency through electrical conduits 131 to electrodes 119. One electrical conduit 131 is grounded for a voltage reference and the other conduit 131 includes current sensor 133, which measures electrical current flow through the conduit. Apparatus 117 also includes controller 83 with electrical conduits 85 and 135 for powering signal generators 77 and 129 respectively, electrical conduits 87 and 137 for monitoring the output voltages of signal generators 77 and 129 respectively, electrical conduits 89 and 139 for monitoring the current flows measured by current sensors 81 and 133 respectively, and electrical conduits 111 and 141 for monitoring temperature measured by thermocouples 63 and 121 respectively.

In operation, to determine the TBN of the used cylinder lubricant, controller 83 powers signal generator 77 through electrical conduit 85 to apply a signal through conduits 79 and electrodes 61 to used cylinder lubricant between the electrodes 61 and powers signal generator 129 through electrical conduit 135 to apply a signal through conduits 131 to fresh cylinder lubricant between electrodes 119. Controller 83, using electrical conduit 111, measures the temperature of the used cylinder lubricant and using electrical conduits 87 and 89 monitors the applied signal to the electrodes 61 and the current flow through the used cylinder lubricant between electrodes 61, measured by current sensor 81, respectively, and from the voltage and current signals calculates the temperature corrected impedance of the used cylinder lubricant. Controller 83 using electrical conduit 141 measures the temperature of the fresh cylinder lubricant and using electrical conduits 137 and 139 monitors the applied signal to the electrodes 119 and the current flow through the used cylinder lubricant between electrodes 119, measured by current sensor 133, respectively, and from the temperature, voltage and current signals calculates the impedance of the fresh cylinder lubricant. A method of this invention uses the temperature corrected impedance data of the fresh and used cylinder lubricants to determine the TBN of the used cylinder lubricant. Controller 83 can further receive information, for example through electrical conduit 99, about concentration and impedance of one or more contaminants present in the used lubricant and a method of this invention can use that information in addition to the temperature corrected impedance data of the fresh and used cylinder lubricants to determine the TBN of the used cylinder lubricant. A method of this invention can communicate information about the used lubricant from controller 83 through electrical conduit 99 as described for apparatus 49 of FIG. 2. Controller 83 can determine TBN of a used lubricant either automatically, when signaled through electrical conduit 99, or when powered "on" through electrical conduit 97. If controller 83 determines used lubricant TBN automatically then the determination can be intermittent or essentially continuous. Controller 83 can essentially continuously monitor the TBN of the used cylinder lubricant flowing through chamber 55 by essentially continuously powering signal generator 77 to apply signals to electrodes 61 and essentially continuously monitoring the used lubricant temperature with thermocouple 63, the applied signal from signal generator 77 and the current flow with current sensor 81. Controller 83 can also essentially continuously monitor the fresh lubricant flowing through conduit 45 by essentially continuously powering signal generator 129 to apply signals to electrodes 119 and essentially continuously monitoring the fresh lubricant temperature with thermocouple 121, the applied signal from generator 129 and the current flow with current sensor 133. To determine the used lubricant TBN, however, controller 83 does not need to monitor the fresh lubricant flowing through conduit 45 each time that the used lubricant is monitored if there is essentially no change in the fresh lubricant since the last time that the fresh lubricant was monitored. Only when there is a change in the fresh lubricant, for example when of fresh lubricant reservoir 37 of FIG. 1 is replenished or when blending cylinder lubricants to vary the TBN of the fresh lubricant to optimize lubricant performance, is monitoring the fresh lubricant necessary to determine the used lubricant base number. That is, the fresh lubricant impedance may be monitored only as needed to determine the fresh lubricant impedance.

While the embodiment of FIG. 4 shows electrodes 119 and thermocouple 121 in conduit 45, in another embodiment the electrodes and thermocouple could be located elsewhere, for example in day reservoir 39 of FIG. 1 or in a separate reservoir, as long as the fresh lubricant between electrodes 119 is essentially the same as the fresh lubricant was pumped into the engine cylinder and became the used cylinder lubricant between electrodes 61.

While the embodiment of FIG. 4 shows multiple signal generators 77, 129, another embodiment may use only one signal generator. Similarly other embodiments may have other components and arrangements as long as either essentially fixed temperature or temperature compensated impedance of the fresh and the used cylinder lubricant can be determined at an appropriate frequency.

FIGS. 2 and 3 show means for determining the concentration of contaminant in the used cylinder lubricant. If the impedance of the system lubricant at the appropriate frequency and temperature is known, that information can be inputted to the controller so that a method of this invention can correct the measured impedance of the used lubricant in volume 57 such that the impedance of the used lubricant without contaminant can be estimated. Other invention embodiments can measure the impedance of the possible contaminant for use in the determination of the used cylinder lubricant TBN.

Figure 5:
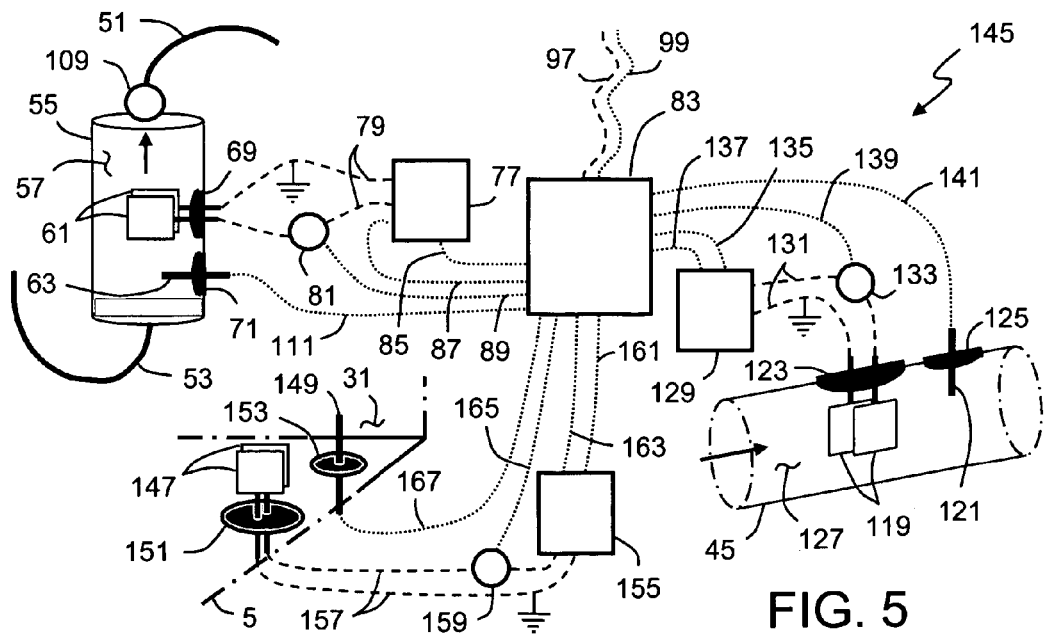
FIG. 5 is a schematic representation of one embodiment of an apparatus of the present invention that applies a first potential to and measures a first response of a fresh lubricant before use, applies a second potential to and measures a second response of the lubricant after use, and applies a third potential and measures a third response of a fluid that can contaminate the used lubricant to determine the base number of the used lubricant.

FIG. 5 is a schematic illustration of another embodiment of apparatus 145 of the present invention that can be used for determining the base number of a used lubricant. For convenience, apparatus elements with the same function as shown in FIGS. 1-4 are numbered the same. Apparatus 145 includes diagnostic chamber 55 with volume 57 that receives and is constantly filled with used lubricant from conduit 53. As previously shown in FIG. 3 and described, apparatus 145 includes electrodes 61, thermocouple 63, signal generator 77, current sensor 81, flow meter 109, and appropriate mounts and electrical conduits for monitoring the impedance and flow rate of the used lubricant in reservoir 55. As previously shown in FIG. 4 and described, apparatus 145 includes electrodes 119, thermocouple 121, signal generator 129, current sensor 133, and appropriate mounts and electrical conduits for monitoring the impedance of the cylinder lubricant before use flowing through volume 127 of conduit 45. Apparatus 145 further includes essentially parallel electrodes 147 and thermocouple 149 that are fixedly held and electrically isolated by mounts 151 and 153 respectively in crankcase 5 (also shown in FIG. 1). Crankcase 5 contains system lubricant 31 that covers electrodes 147 and thermocouple 149. Apparatus 145 includes signal generator 155 that supplies a voltage signal of fixed amplitude and frequency through electrical conduits 157 to electrodes 147 with one conduit 157 grounded and the other conduit 157 includes current sensor 159, which measures electrical current flow through the conduit. Apparatus 145 includes conduits 161 and 163 for controller 83 to power signal generator 155 and conduits 165 and 167 for controller 83 to monitor current flows measured by sensor 159 and temperature measured by thermocouple 155 respectively.

To determine the TBN of the used cylinder lubricant, controller 83 powers signal generators 77, 129 and 155 to apply signals when appropriate, monitors resulting currents measured by current sensors 81, 133 and 159 respectively, and monitors temperatures measured by thermocouples 63, 121, 149 respectively and calculates the temperature corrected impedance of the used lubricant from the engine cylinder, the fresh cylinder lubricant before use and the system lubricant respectively. Controller 83 also monitors the used lubricant flow through reservoir 55 measured by flow meter 109 and determines the concentration of contaminant in the used cylinder lubricant as previously described. The method of this invention uses temperature corrected impedance data and the concentration of contaminant to determine the TBN of the used cylinder lubricant and to communicate information about the used lubricant from controller 83 through electrical conduit 99 as previously described.

As described for embodiments shown in FIGS. 2, 3 and 4, other embodiments can eliminate one or more of the thermocouples 63, 121, and 149 if lubricant temperature is known by other means. Other embodiments may use less than three signal generators of current sensors to apply signals and measure current responses from electrode pairs 61, 119 and 147. Other embodiments may have other components and arrangements as long as the appropriate fixed temperature or temperature compensated impedances and concentration of contamination can be determined for the determination and communication of information about the TBN of the used cylinder lubricant.

Also as described with reference to the embodiment shown in FIG. 4, the system lubricant impedance does not need to be determined each time the TBN of the used lubricant is determined. Only when there is contamination of the used cylinder lubricant with system lubricant is the impedance of the system lubricant needed. Hence, the system lubricant impedance may be monitored only as needed when determining the base number of the used cylinder lubricant.

Figure 6:
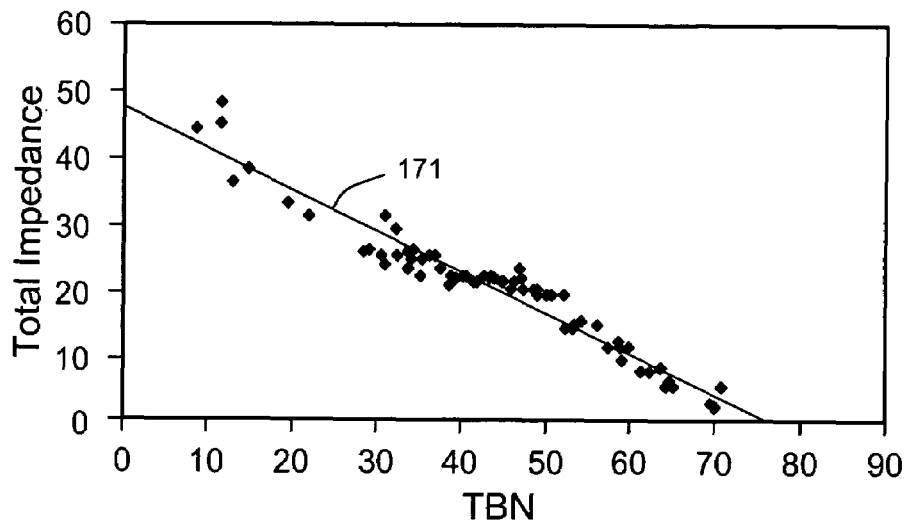
FIG. 6 is a graphic representation of fresh and used lubricant total impedance as a function of laboratory determined total base number (TBN).

FIG. 6 shows the about 10 Hz total impedance $Z_T$ in mega ohms (M$\Omega$) electrodes versus TBN of approximately 70 TBN cylinder lubricants before use and after use in a slow-speed, two-stroke diesel engine of crosshead construction. TBN was measured in the laboratory using ASTM D2896 method. Electrical impedance was measured in the laboratory at about 35° C. using essentially parallel plate electrodes about 3.14 cm$^2$ separated by 0.1 mm. The unused fresh 70 TBN lubricants were BP Energol CLO 50M, ChevronTexaco TARO® Special HT70, and ExxonMobil Mobilgard® 570. The used cylinder lubricants were removed from the cylinders of various engines, using the above 70 TBN lubricants, various fuels and operating under variety of operating conditions and cylinder lubricant feed rates. The samples contained essentially no system lubricant. The linear best-fit line 171 has an R$^2$ of 0.94. In applications where only currently available 70 TBN cylinder lubricants are used and where there is no system lubricant contamination, the used cylinder lubricant TBN can be determined, that is estimated, by the equation:

$$TBN=76-1.6 \times Z_T,$$

where $Z_T$ is either the about 10 Hz total impedance in M$\Omega$ measured at about 35° C. with about 3.14 cm$^2$ parallel plate electrodes or measured at another temperature and corrected to about 35° C.

Figure 7:
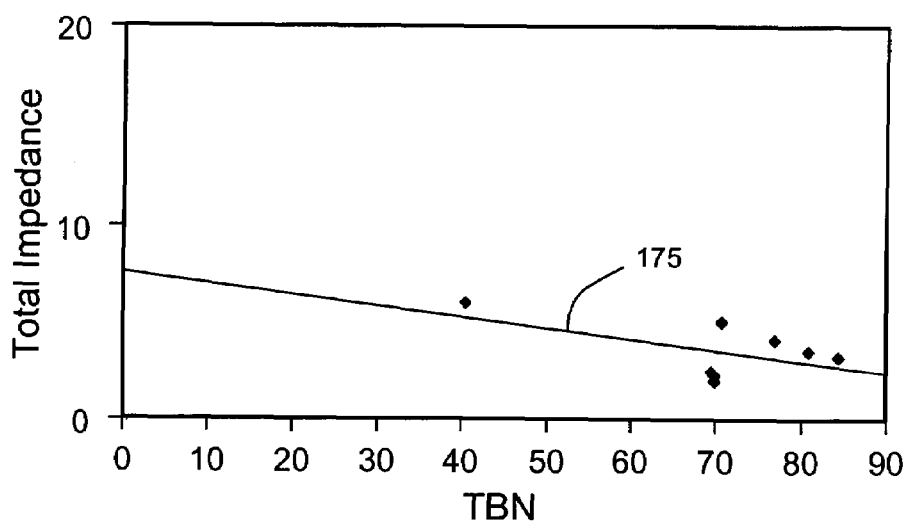
FIG. 7 is a graphic representation of fresh lubricant total impedance as a function of laboratory determined TBN.

FIG. 7 shows the total impedance $Z_{Ti}$ in M$\Omega$ electrodes versus TBN$_i$ of unused cylinder lubricants, where the subscript "i" designates the initial total impedance and TBN of the lubricant. TBN$_i$ and $Z_{Ti}$ were measured as described above. The samples contained no system lubricant. Line 175 is the linear best fit line, which is consistent with all lubricants shown having relatively similar formulation in that most of the base is in the form of calcium carbonate supplied as overbased detergents. Lubricants formulated from other components may not fall along line 175. In any case, when any cylinder lubricant is used, the total impedance $Z_T$ versus TBN of the unused and the used lubricants can be described by a function "F" of the measured total impedance such that TBN=F($Z_T$, $Z_{Ti}$). In many cases, over most of the TBN range of interest, the function "F" can be approximated as linear in $Z_T$ with the coefficients determined by the initial impedance $Z_{Ti}$, such that:

$$TBN=G(Z_{Ti}) \times Z_T + H(Z_{Ti}).$$

The coefficient of the linear function could also be functions the initial TBN$_i$ or of $Z_{Ti}$ and TBN$_i$.

Figure 8:
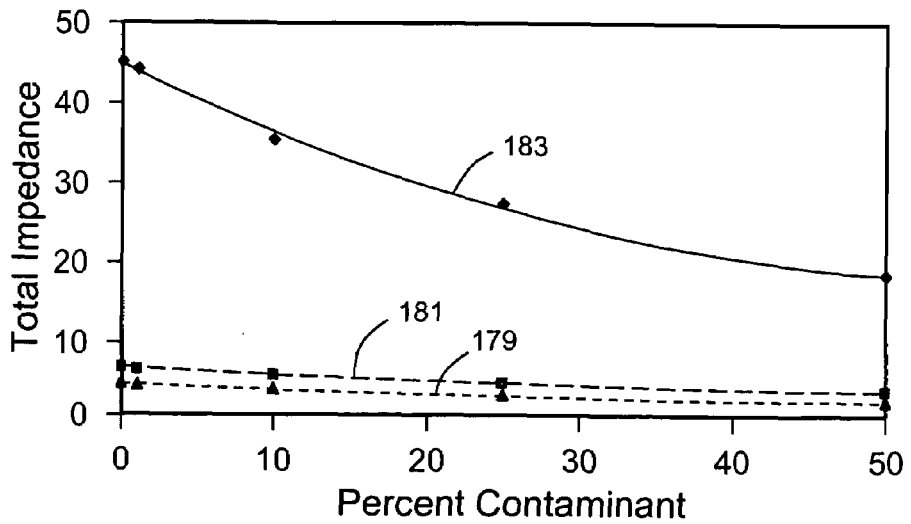
FIG. 8 is a graphic representation of fresh and used lubricant total impedance as a function of percentage contamination.

FIG. 8 shows the total impedance $Z_T$ in M$\Omega$ of cylinder lubricants as a function of the percentage of system lubricant contamination for unused lubricants of 75 TBN and 40 TBN and a used lubricant of 4 TBN which in the figure are connected with lines 179, 181 and 183 respectively. The total impedance $Z_T$ of system lubricant measured in the laboratory under the same conditions as the contaminated and uncontaminated cylinder lubricant is 34 M$\Omega$. Despite the system lubricant having higher impedance than the 40 TBN and 75 TBN cylinder lubricants, $Z_T$ decreases as a function of system lubricant contaminant. The 4 TBN used lubricant has total impedance greater than the system lubricant; however, even for this lubricant the total impedance decrease as a function of contamination is greater than expected assuming a simple rule of mixtures where a mixture of fluid A with impedance $Z_A$ and fluid B with impedance $Z_B$ is equal to $Z^{A+B}=[(1-\alpha)/Z_A + \alpha/Z_B]^{-1}$ where $\alpha$ is the ratio of the volume of fluid B to the total volume of fluid A plus fluid B. Instead the measure resistance for each lubricant with contaminant is better described where the conductivity of the combined fluid is modeled as a random resistor network (for reference and incorporated herein see "Modeling of Conductivity in Composites with Random Resistor Networks" by Maciej Siekierski and Katarzyna Nadara, Electrochimica Acta 50 (2005) 3796-3804) for relatively low concentrations of a contaminant. Using this model, the impedance of the total fluid can be modeled by:

$$Z_{A+B} = [(1-\alpha)/Z_A + 3 \times \alpha/Z_A + \alpha/Z_B]^{-1},$$

where the coefficient for the second term was determined by an empirical fit to the data.

FIG. 9 shows a table comparing the measured total impedance (Meas.) of the used lubricant, the impedance calculated using a mixture (Mix.) of the cylinder and system lubricants, and the impedance calculated with the random network (R.N.) equation. The random network impedance model has good correlation with the measured impedance for the three cylinder lubricants listed above. This correlation between the measured and calculated impedance allows for a function that estimates the actual impedance of a used lubricant knowing the measured impedance of the lubricant removed from a cylinder, the concentration of system lubricant contained in the removed lubricant and the impedance of the system lubricant. In general, $Z_T$ of the used lubricant can be estimated by a function "G" such that $Z_T = G(Z_M, Z_S, \%)$ where $Z_M$ is the measured impedance, $Z_S$ is the impedance of the system lubricant, and % is the percentage concentration of the contaminant in the measured used lubricant. As previously described, the ratio of flow rate of used lubricant out $V_o$ of the open lubricating system to the flow rate of fresh lubricant into $V_i$ the system can be used to estimate the percentage contaminant in the used lubricant knowing the typical amount of lubricant that is lost, that is consumed or leaked, during equipment operation. Indeed, the function "G" does not have to be dependent on the percentage contaminant, but can be dependent on any property that allows the percentage contaminant to be estimated or determined.

FIG. 10 shows an embodiment 187 of a feature of the present invention that uses the total impedance $Z_T$ of the used cylinder lubricant and the total impedance $Z_{Ti}$ of the fresh lubricant to determine the base number of a used lubricant in an open lubricant system where the used lubricant is maintained at a relatively constant temperature for condition determination, where there is essentially no contamination of the used lubricant, and where $Z_{Ti}$ is inputted to the method if impedance of the unused lubricant changes. The used lubricant temperature can be maintained either by an apparatus of this invention, for example temperature controller 101 of apparatus 49 in FIG. 2, or by a means associated with the equipment in which the lubricant is used.

Method 187 begins in block 189 each time the equipment is started, i.e. turned "on". After start-up method 187 proceeds to block 191, to read the used lubricant impedance $Z_T$. $Z_T$ is obtained by a lubricant measurement apparatus that applies a voltage signal at the appropriate frequency to a used lubricant between electrodes and measures the applied voltage and the resulting current as described with reference to the apparatuses shown in FIGS. 2 and 3. The signal read in block 191 can be the actual $Z_T$ of the used lubricant, or measured values that can be converted to $Z_T$. $Z_T$ can be data collected by the apparatus over a short period of time with no filtering, or can be averaged over a longer period of time and averaged and/or filtered to minimize noise and to better quantify the lubricant's electrical response. In any case, while the equipment is "on" method 187 reads $Z_T$ in block 191 at fixed intervals of "X" minutes to determine the used lubricant base number. In block 193, method 187 determines if a fresh, that is before use, lubricant is being used since the last time $Z_T$ was read. This determination can be made, for example by controller 83 of FIGS. 2 and 3 receiving an input via electrical conduit 99 that the impedance of the fresh lubricant has changed, and if the determination of block 193 is "yes", method 187 in block 195 reads the impedance of the new fresh lubricant $Z_{Ti}$, which can be inputted for example through conduit 99 to controller 83 of FIG. 2. Using either the impedance of a new $Z_{Ti}$ if the determination in block 193 is "yes", or the previous $Z_{Ti}$ method 187 in block 199 determines the TBN of the used lubricant using a function "F" of the used lubricant $Z_T$ and the fresh lubricant $Z_{Ti}$ as was described with reference to FIG. 7. Method 187 outputs the determined TBN in block 199 to, for example, a signaling device that can be read by an equipment operator or maintenance personnel, a signal processor that can use the information to control the equipment or to control the fresh lubricant being pumped to the equipment, or a memory where it can later be retrieved. After outputting the TBN information in block 199, method 187 returns to block 191 where "X" minutes after the previous reading, the method again reads the impedance of the used lubricant and begins the steps of determining and outputting the waste lubricant TBN. In this manner, method 187 essentially continuously monitors the TBN of the used, that is waste, lubricant.

While method 187 is shown to provide a TBN output essentially continuously every "X" seconds during equipment operation, another embodiment of the present invention can operate only when receiving an external input to provide a TBN output.

While the method 187 is shown with the calculated TBN being a function "F" of $Z_T$ and $Z_{Ti}$, another embodiment of a method of the present invention can be for an application where the fresh lubricant is essentially always the same, that is, where $Z_{Ti}$, is essentially fixed. For such a method, the used lubricant TBN can be calculated as a function of $Z_T$ only. Similarly another method can calculate the TBN of the used lubricant using $Z_T$ and $TBN_i$, the TBN of the fresh lubricant, or can calculate the TBN of the used lubricant using $Z_T$, $Z_{Ti}$ and $TBN_i$, where $TBN_i$ or $Z_{Ti}$ and $TBN_i$ are read when an input is provided that a new lubricant is being used.

Method 187 is described with the impedance of the fresh lubricant $Z_{Ti}$, being read in block 195 from an input to an apparatus controller. Another embodiment of a method of this invention, however, can read the fresh lubricant impedance $Z_{Ti}$ using apparatus, for example as shown in FIG. 4, that includes electrodes immersed in the fresh lubricant and means for applying a signal and measuring a response at an appropriate frequency to determine $Z_{Ti}$ each time a positive response is obtained in block 193. In another embodiment, $Z_{Ti}$ can be read each time that $Z_T$ is read.

Method 187 is shown and described with the used cylinder lubricant maintained at a relatively fixed temperature for TBN determination. Another embodiment of a method of this invention, however, can compensate the measured impedances for lubricant temperature variations as impedance is being measure.

FIG. 11 shows an embodiment 203 of a feature of the present invention that uses the total impedance $Z_T$ of the used lubricant measured at temperature T, and the total impedance $Z_{Ti}$ of the fresh lubricant measured at temperature $T_i$ to determine the base number of a used cylinder lubricant. The impedances and temperatures are measured by an apparatus of this invention, for example apparatus 117 shown in FIG. 4. For convenience, method blocks with the same function as shown in FIG. 10 are numbered the same.

Method 203 begins in block 189 each time the equipment is started and proceeds to block 205 to read the used lubricant total impedance $Z_T$, the used lubricant temperature T, the fresh lubricant total impedance $Z_{Ti}$, and the fresh lubricant temperature $T_i$. The $Z_T$ and $Z_{Ti}$ can be actual impedances or measured values that can be converted to $Z_T$ and $Z_{Ti}$. Similarly T and $T_i$ can be actual temperatures or temperature equivalents. The values read in block 205 can be essentially instantaneous measurements or can be averaged and/or filtered over a longer period of time. In any case, after reading the values in block 205, method 203 in block 207 compensates the impedances $Z_T$ and $Z_{Ti}$ using temperatures T and Ti respectively using function "h" and "k" respectively, such that the temperature compensated $Z_{TC}$ and $Z_{TiC}$ are effectively the total impedances that would be measured if the used and fresh lubricants respectively were held fixed at temperature "C". In block 209, method 203 determines the TBN of the used lubricant using a function "$F_C$" of the temperature compensated total impedances $Z_{TC}$ and $Z_{TiC}$. Method 203 outputs the determined TBN in block 199 to, for example, a signaling device that can be read by an equipment operator or maintenance personnel, a signal processor that can use the information to control the equipment or to control the unused lubricant being pumped to the equipment, or a memory where it can later be retrieved. After outputting the TBN information in block 199, method 203 returns to block 205 where "X" minutes after the previous reading, the method again reads the impedance of the used lubricant and begins the steps of determining and outputting the waste lubricant TBN. In this manner, method 203 essentially continuously monitors the TBN of the waste lubricant.

While method 203 is shown to provide a TBN output essentially continuously every "X" seconds during equipment operation, another embodiment of the present invention can operate only when receiving an external input to provide a TBN output.

The embodiments shown in FIGS. 10 and 11 provide correct TBN output for used lubricants that contain essentially no contaminant since as shown and described with reference to FIG. 8, a contaminant can substantially affect the measured total impedance of the used lubricant exiting equipment.

Figure 12:
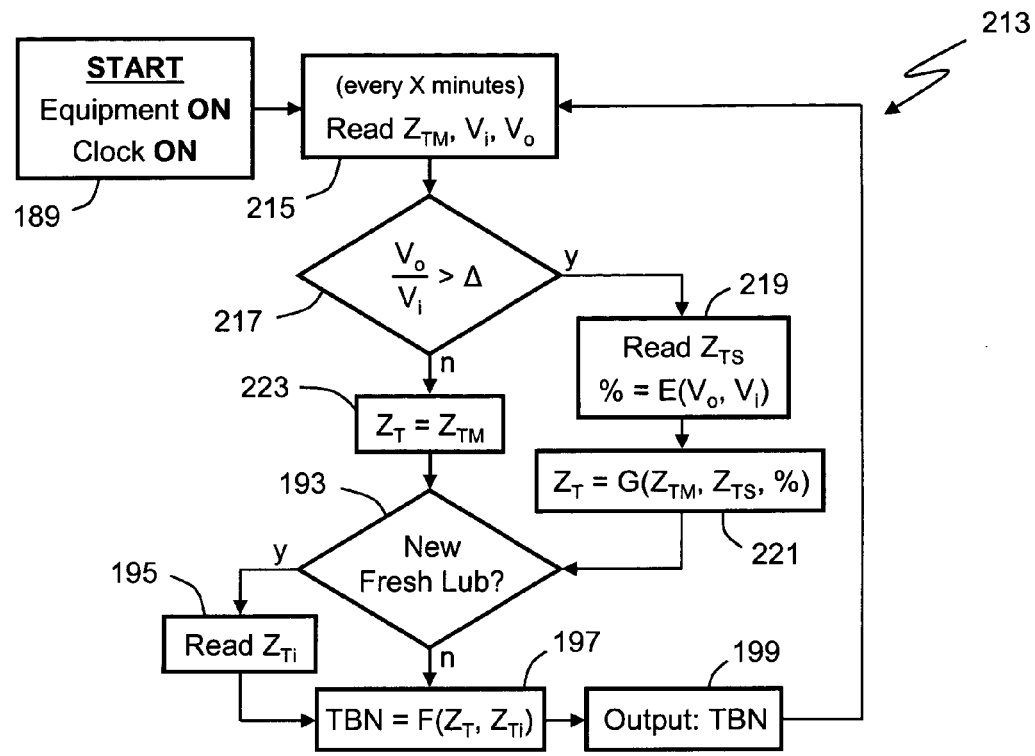
FIG. 12 is a flow chart of a feature of a method of the present invention wherein the used lubricant total impedance, fresh lubricant total impedance and the amount of a contaminant in the used lubricant are used to determine the used lubricant TBN.

FIG. 12 shows an embodiment 213 of a feature of the present invention that uses the measured total impedance $Z_{TM}$ of the used lubricant, the total impedance $Z_{Ti}$ of the fresh lubricant, the total impedance $Z_S$ of a possible contaminant in the used lubricant, and the percentage contaminant % based on the ratio of fresh lubricant flowing into the open lubricating system $V_i$ to the used lubricant flowing out of the system $V_o$ to determine the base number of a used lubricant where the used cylinder lubricant is maintained at a relatively constant temperature for condition determination, where $Z_{Ti}$ is inputted if impedance of the unused lubricant changes, and where $Z_S$ is inputted if contamination is detected. The used lubricant temperature can be maintained either by an apparatus of this invention, for example temperature controller 101 of apparatus 49 in FIG. 2, or by a means associated with the equipment in which the lubricant is used. The flow rate $V_o$ of the used lubricant can be input either by an apparatus of this invention, for example the time to fill a volume as described with reference to FIG. 2 or using a flow meter as described with reference to FIG. 3, or by a means associated with the equipment in which the lubricant is used. The flow rate $V_i$ of the fresh lubricant can be input either by an apparatus of this invention, for example a flow meter or by a means, for example one that is based on equipment speed, power output or lubricant pump rate, associated with the equipment in which the lubricant is used. For convenience, method blocks with the same function as shown in FIGS. 10 or 11 are numbered the same.

Method 213 begins in block 189 each time the equipment is started and proceeds to block 215 where $Z_{TM}$, $V_i$ and $V_o$ are read. $Z_{TM}$ is the measured used lubricant total impedance or total impedance equivalent, and $V_i$ and $V_o$ are the used and fresh lubricant flow rates, flow rate equivalents, or data that can be used to calculate the appropriate flow rates. The values read in block 215 can be essentially instantaneous measurements or can be averages. In block 217 method 213 determines if the ratio of the flow rate $V_o$ of used lubricant out of the equipment to the flow rate $V_i$ of fresh lubricant into the equipment is greater than Δ. In the case where the equipment does not consume, for example burn, any of the lubricant during use, Δ could be set equal to one. Most equipment, however, consumes some lubricant, thus Δ is typically set to a number less than one, and although not shown in this embodiment, another embodiment can have a Δ that is a function of equipment operation variables to account for variations in lubricant consumption as a function of equipment operation. If the determination of block 217 is "yes", which means that a contaminant is present since the used lubricant flow rate is greater than expected, method 213 in block 219 reads the total impedance $Z_{TS}$ of the contaminant, which in the case of the two-stroke diesel engine is the system lubricant, and determines, that is estimates, the percentage contamination % using a function "E" of the $V_o$ and $V_i$. The function "E", for example in the case where there is not lubricant consumption in the open lubricating system, that is where $V_o$ would equal $V_i$ with no contamination, could be, $$E(V_o,V_i)=100\times(V_o-V_i)/V_o=\%.$$

The $Z_{TS}$ can be inputted for example through conduit 99 to controller 83 of FIG. 2 or can be measured for example using electrodes 147, signal generator 155, current meter 159 and controller 83 of FIG. 5. Method 213 in block 221 estimates the actual total impedance $Z_T$ of the used lubricant without contaminant with function "G" of the measured total impedance $Z_{TM}$ of the used lubricant, the impedance of the contaminant $Z_{TS}$ and the percentage contaminant % as was described with reference to FIG. 8 and Table 1. If the determination of block 217 is "no", which means that there is essentially no contaminant present, method 213 in block 223 sets the total impedance $Z_T$ of the used lubricant equal to the measured impedance $Z_{TM}$. Once $Z_T$ is determined either in block 221 or 223, method 213 determines, as in method 187 of FIG. 10, if the fresh lubricant has been changed in block 193. If the determination is "yes", in block 195 method 213 reads a new total impedance $Z_{Ti}$ of the fresh lubricant, or if the determination is "no" the previous total impedance $Z_{Ti}$ is retained, such that in block 197 the TBN of the used lubricant is determined and in block 199 method 213 output the determined TBN. After outputting the TBN information in block 199, method 213 returns to block 215 where "X" minutes after the previous reading, the method again reads the impedance of the used lubricant and begins the steps of determining outputting the used lubricant TBN. In this manner, method 213 essentially continuously monitors the TBN of the used lubricant.

While method 213 is shown with the estimated $Z_T$ in block 221 being a function of $Z_{TS}$, which is read in block 219, another embodiment of a method of the present invention can be for an application where the contaminant has a total impedance $Z_{TS}$ that is essentially fixed. For such a method, the used lubricant total impedance $Z_T$ can be estimated as a function of the measured total impedance $Z_{TM}$ and percentage contaminant % only.

While not shown in method 213, in another embodiment, if the determination in block 217 is "yes", in addition to estimating the actual total impedance $Z_T$ before advancing to block 193, a method can provide an output to, for example, a signaling device that can be read by an equipment operator or maintenance personnel, a signal processor that can use the information to control the equipment, or a memory where it can later be retrieved, that contaminant is present and/or the concentration of contaminant present in the used lubricant.

Method 213 is shown and described with the used lubricant, the fresh lubricant and the contaminant maintained at a relatively fixed temperature for the TBN determination. Another embodiment of a method of this invention, however, can compensate the measured impedances for temperature variations as the impedances are being measured.

Figure 13:
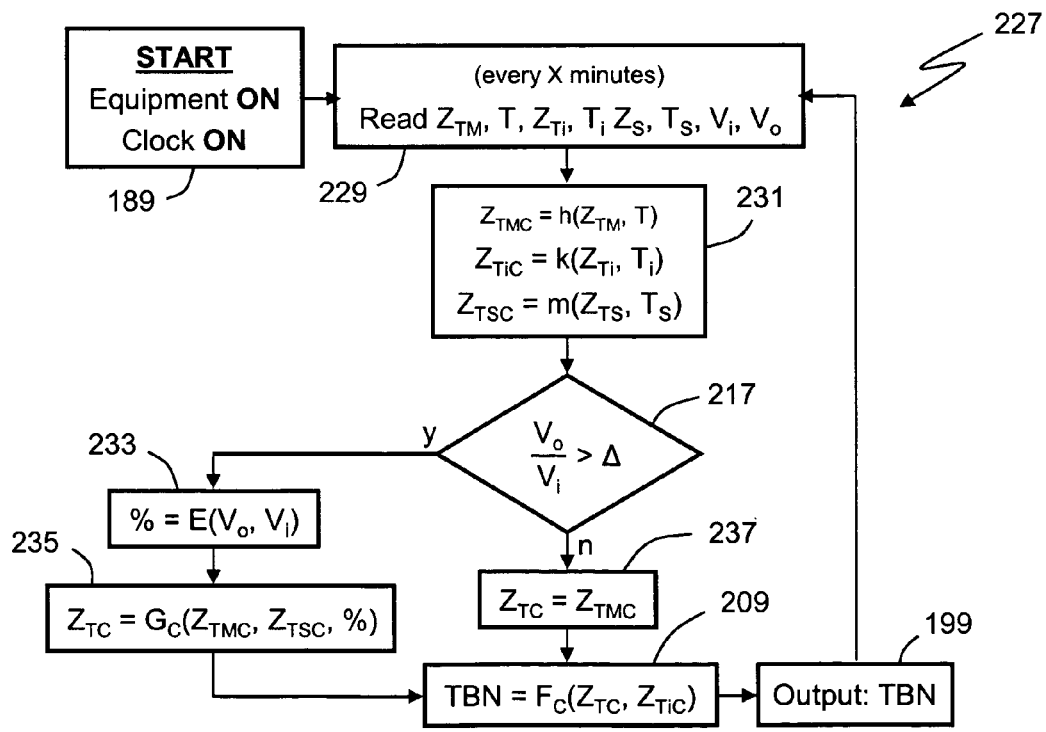
FIG. 13 is a flow chart of a feature of a method of the present invention wherein used lubricant total impedance, fresh lubricant total impedance, contaminant total impedance are temperature compensated and together with the amount of a contaminant in the used lubricant are used to determine the used lubricant TBN.

FIG. 13 shows an embodiment 227 of a feature of the present invention that uses the measured total impedance $Z_{TM}$ of the used lubricant at temperature T, the total impedance $Z_{Ti}$ of the fresh lubricant at temperature $T_i$, the total impedance of a possible contaminant in the used lubricant $Z_S$ at temperature $T_S$, and the percentage contaminant % based on the ratio of fresh lubricant flowing into the open lubricating system $V_i$ to the used lubricant flowing out of the system $V_o$ to determine the base number of a used lubricant. The impedances, temperatures output flow rates can be measured by an apparatus of this invention, for example apparatus 145 shown in FIG. 5. For convenience, method blocks with the same function as shown in FIGS. 10, 11 or 12 are numbered the same.

Method 227 begins in block 189 each time the equipment is started and proceeds to block 229 to read the measured used lubricant total impedance $Z_{TM}$, the used lubricant temperature T, the fresh lubricant total impedance $Z_{Ti}$, the fresh lubricant temperature $T_i$, the possible contaminant total impedance $Z_{TS}$, the possible contaminant temperature $T_S$, the flow rate $V_i$ of the fresh lubricant into the equipment, and the flow $V_o$ rate of the used lubricant out of the equipment. The impedances $Z_{TM}$, $Z_{Ti}$, and $Z_{TS}$ can be actual impedances or impedance equivalents or measured values that can be converted to impedances. Similarly, T $T_i$, and $T_S$ can be actual temperatures or temperature equivalents, and $V_i$ and $V_o$ can be actual flow rates or flow rate equivalents. The values read in block 229 can be essentially instantaneous measurements or can be averaged and/or filtered over a longer period of time. In any case, after reading the values in block 229, method 227 compensates the impedances $Z_{TM}$, $Z_{Ti}$, and $Z_{TS}$ using temperatures T $T_i$, and $T_S$ respectively using functions "h", "k" and "m" respectively, such that the temperature compensated $Z_{TMC}$, $Z_{TiC}$, and $Z_{TSC}$ are effectively the total impedances that would be measured if the lubricants and contaminant were held fixed at temperature "C". In block 217 method 227 determines if the shown ratio of the flow rates is greater than Δ. If the determination of block 217 is "yes", which means that a contaminant is present, method 227 in block 233 determines or estimates the percentage contamination % using a function "E" as described for method 231 of FIG. 12. In block 235 method 227 estimates the actual temperature compensated total impedance $Z_{TC}$ of the used lubricant without contaminant with function "$G_C$" of the temperature compensated measured total impedance $Z_{TMC}$ of the used lubricant, the temperature compensated total impedance of the contaminant $Z_{TSC}$ and the percentage contamination %, as described with reference to FIG. 8 and Table 1. If the determination of block 217 is "no", which means that there is essentially no contaminant present, method 227 in block 237 sets the temperature compensated total impedance $Z_{TC}$ of the used lubricant equal to the temperature compensated measured impedance $Z_{TMC}$. Once $Z_{TC}$ is determined either in block 233 or 235, method 227 determines, as in method 203 of FIG. 11, the TBN of the used lubricant in block 209 and in block 199 outputs the determined TBN. After outputting the TBN information in block 199, method 227 returns to block 215 where "X" minutes after the previous reading, the method again reads the listed total impedances, temperatures and flow rates and begins the steps of determining outputting the waste lubricant TBN. In this manner, method 227 essentially continuously monitors the TBN of the waste lubricant.

While embodiment 227 of FIG. 13 monitors the used lubricant TBN essentially continuously when the equipment is "on", in another embodiment a method of this invention can determine the used lubricant TBN only when receiving an input, for example from an operator, a service technician of from another controller, to do so.

While embodiment 227 of FIG. 13 shows all three measured total impedances being temperature compensated, in another embodiment, a method of this invention may only need to temperature compensate one of the impedances if the other two temperatures are held relatively fixed; and in another embodiment only two impedances may be temperature compensated if the other temperature is held at a relatively fixed.

While apparatuses in 49, 107, 145 in FIGS. 2, 3, 5 respectively, and methods 213 and 227 in FIGS. 12 and 13 are shown and described using flow rates as the means for determining if the used lubricant is contaminated and for estimating the total impedance of a used lubricant without contamination. In other embodiments information about presence and concentration of contamination can be entered, for example by electrical conduit 99 to controller 83, or other means can be used to determine presence and amount of contaminants, as was previously described.

While particular embodiments of the present invention have been shown and described, it is apparent that various combinations, changes and modification may be made therein to meet used lubricant TBN determination needs of various applications without departing from the invention in its broadest aspects. In particular, with regard to various functions performed by the above described invention, the terms (including any reference to a "means") used to describe individual components or sub-systems of the invention are intended to correspond, unless otherwise indicated, to any component or sub-system which performs the specified function of the described component or sub-system (e.g. that is functionally equivalent), even though not structurally or electronically equivalent to the described component or sub-system which performs the function in the herein illustrated embodiments of the invention. In addition, while a particular feature of the invention may have been disclosed with respect to only one of several embodiments, such feature may be combined with one or more other features of the other embodiments as may be desired and advantageous for any given or particular application.

What is claimed is:

1. A method for determining the total base number of a used lubricant from an open, all-loss, lubricating system comprising:
   a) applying an AC voltage signal between electrodes immersed in the used lubricant,
   b) measuring the used lubricant dependent response to the applied signal, and
   c) determining the used lubricant base number from the measured response;
   wherein the method further includes the steps of at least one of the following selected from the group consisting of:
   i) receiving input of the total impedance or impedance equivalent of the fresh lubricant,
   ii) receiving input of the TBN or TBN equivalent of the fresh lubricant,
   iii) applying a second AC voltage signal between electrodes immersed in the fresh lubricant and measuring the fresh lubricant dependent response to the applied second signal,
   and combinations there of, for use in determining the used lubricant's base number.

2. The method of claim 1 wherein the frequency of the applied signal is predetermined as a function of at least one of the following selected from the group consisting of electrode geometry, lubricant temperature, lubricant temperature range, composition of the lubricant being monitored and combinations thereof, and the measured response is at least one of the following selected from the group consisting of total impedance, total impedance equivalent, data that used to calculate total impedance and combinations thereof.

3. The method of claim 1 where the applied AC voltage is between 0.1 and 1000 Hz.

4. The method of claim 1 that further includes the step of measuring the used lubricant temperature and compensating the lubricant dependent response for variations in the used lubricant temperature.

5. The method of claim 1 that further includes the step of controlling the temperature of the used lubricant to a desired temperature before applying the electrical potential and measuring the resulting electrical response.

6. The method of claim 1 wherein the frequencies of the applied signals are predetermined as a function of at least one of the following selected from the group consisting of individual electrode geometry, individual lubricant temperature, individual lubricant temperature range, composition of the lubricant being monitored and combinations thereof, and the measured responses are at least one of the following selected from the group consisting of total impedance, total impedance equivalent, data that used to calculate total impedance and combinations thereof.

7. The method of claim 1 where the applied AC voltages are between 0.1 and 1000 Hz.

8. The method of claim 1 that further includes at least one of the following steps selected from the group consisting of measuring the used lubricant temperature, and compensating the used lubricant dependent response for variations in the used lubricant temperature, measuring the fresh lubricant temperature, and compensating the fresh lubricant dependent response for variations in the fresh lubricant temperature, and combinations thereof.

9. The method of claim 1 that further includes the steps of at least one of the following selected from the group consisting of:
   i) receiving input of the percentage concentration of contaminate in the used lubricant,
   ii) receiving input of the total impedance or total impedance equivalent of a potential contaminant,
   iii) receiving input of properties that allow the determination of the percentage concentration of contaminant in the used lubricant,
   iv) measuring properties that allow the determination of the percentage concentration of contaminant in the used lubricant,
   v) measuring a third response to a third applied AC voltage signal between electrodes immersed in a potential contaminant,
   vi) correcting the measured used lubricant response for the percentage concentration and total impedance of contaminant,
   and combinations thereof, for use in determining the used lubricant's base number.

10. The method of claim 9 wherein the properties that allow determination of the percentage concentration of contaminant in the used lubricant are flow rate of fresh lubricant into the open lubricating system and the flow rate of used lubricant out of the system.

11. The method of claim 9 wherein the frequencies of the third applied signals are predetermined as a function of at least one of the following selected from the group consisting of individual electrode geometry, individual lubricant temperature, individual lubricant temperature range, composition of the lubricant being monitored and combinations thereof, and the measured responses are at least one of the following selected from the group consisting of total impedance, total impedance equivalent, data that used to calculate total impedance and combinations thereof.

12. The method of claim 9 where the applied AC voltages are between 0.1 and 1000 Hz.

13. The method of claim 9 that further includes at least one of the following steps selected from the group consisting of measuring the used lubricant temperature, and compensating the used lubricant dependent response for variations in the used lubricant temperature, measuring the contaminant temperature, and compensating the fresh lubricant dependent response for variations in the fresh lubricant temperature, and combinations thereof.

14. An apparatus to monitor the total base number of a used lubricant from an open, all-loss, lubricating system comprising:
   a) at least one pair of separated electrodes that are immersed in a used lubricant being monitored;
   b) at least one signal generator that applies an AC voltage to the electrodes;
   c) at least one monitor that measures a used lubricant dependent electrical response to the applied signal; and
   d) a controller that can analyzes applied electrical signal and corresponding measured electrical response to determine the TBN of the used lubricant;
   wherein the apparatus further includes a means for the controller to determine the percentage contaminant or equivalent that may be present in the used lubricant.

15. The apparatus of claim 14 wherein the controller is further capable of at least one of the following selected form the group consisting of receiving information that can be used in the determination of the TBN of the used lubricant, outputting information about the used lubricant TBN determination, and combination thereof.

16. The apparatus of claim 14 wherein the electrical response monitor is a current sensor, which measures a current generated in response to the applied signal.

17. The apparatus of claim 14 wherein the controller controls the signal generator.

18. The apparatus of claim 14 that further includes a temperature sensor that monitors a temperature of the used lubricant.

19. The apparatus of claim 18 that further includes a means to compensate the determined used lubricant TBN with the monitored temperature.

20. The apparatus of claim 14 that further includes a temperature control means for regulating the temperature of the used lubricant being monitored.

21. The apparatus of claim 14 that further includes:
   i) at least one pair of separated electrodes that are immersed in the fresh lubricant;
   ii) at least one signal generator that applies an AC voltage to the electrodes; and
   iii) at least one monitor that measures a fresh lubricant electrical response to the applied signal.

22. The apparatus of claim 14 that further includes a means for the controller to determine when there is a change in the fresh lubricant.

23. The apparatus of claim 14 wherein the means for determining the percentage contaminant or equivalent include at least one of the following selected from the group consisting of receiving information about the flow rate or equivalent of fresh lubricant into the open lubricating system, receiving information about the flow rate or equivalent of used lubricant out of the open lubricating system, measuring the flow rate or equivalent of fresh lubricant into the open lubricating system, measuring the flow rate or equivalent of used lubricant out of the open lubricating system, and combinations thereof.

24. The apparatus of claim 14 that further includes a means for the controller to determine the total impedance or equivalent of a potential contaminant.

25. The apparatus of claim 24 wherein the means for determining contaminant total impedance or equivalent comprises:
   i) at least one pair of separated electrodes that are immersed in the contaminant;
   ii) at least one signal generator that applies an AC voltage to the electrodes; and
   iii) at least one monitor that measures a contaminant electrical response to the applied signal.

* * * * *